United States Patent [19]

Katsura

[11] Patent Number: 4,919,802
[45] Date of Patent: Apr. 24, 1990

[54] BLOOD FILTER

[75] Inventor: Yoshiro Katsura, Fuji, Japan

[73] Assignee: Terumo Kabushiki Kaisha, Tokyo, Japan

[21] Appl. No.: 278,001

[22] Filed: Nov. 30, 1988

[30] Foreign Application Priority Data

Dec. 4, 1987 [JP] Japan .................. 62-307032

[51] Int. Cl.$^5$ .................. B01D 19/00; B01D 35/30
[52] U.S. Cl. .................. 210/188; 55/204; 210/304; 210/436; 210/456; 210/472; 210/512.1
[58] Field of Search .................. 55/204; 210/304, 349, 210/436, 456, 472, 512.1, 188; 604/4

[56] References Cited

U.S. PATENT DOCUMENTS

| Re. 32,711 | 7/1988 | Dickens et al. | 210/472 |
| 3,795,088 | 3/1974 | Esmond | 210/436 |
| 3,827,562 | 8/1974 | Esmond | 210/304 |
| 4,345,919 | 8/1982 | Wilkinson et al. | 210/436 |
| 4,490,254 | 12/1984 | Gordon et al. | 210/436 |
| 4,690,762 | 9/1987 | Katsura | 210/436 |
| 4,758,377 | 7/1988 | Köhn et al. | 210/472 |

FOREIGN PATENT DOCUMENTS 2452936 12/1980 France .................. 210/472

Primary Examiner—W. Gary Jones
Attorney, Agent, or Firm—Frishauf, Holtz, Goodman & Woodward

[57] ABSTRACT

A blood filter having a bubble separating section includes a generally cylindrical chamber for allowing bubbles to separate from blood, an air discharging vent at an upper end of the chamber, and an inlet conduit horizontally extending from the chamber for introducing blood into the chamber. A blood filter section is disposed below the bubble separating section, including an outlet at a lower end for discharging blood and a filter member disposed between the inlet and the outlet. The axis of the inlet conduit extends substantially parallel to a tangent line of the generally circular chamber at the connection between the chamber and the inlet conduit, but is spaced a certain distance from the tangent line in a plane perpendicular to the axis of the chamber. An inflow portion is disposed between the inlet conduit and the chamber so as to define a flowpath merging the inlet conduit to the chamber, whereby the inflow portion directs incoming blood from the inlet conduit so as to flow as a substantial laminar flow to a swirl flow of blood in the chamber and then merge with the swirl flow. The apparatus has high bubble removal capacity in that few bubbles are conveyed to the filter member since newly introduced blood does not disturb the existing swirl flow of blood in the chamber.

8 Claims, 8 Drawing Sheets

BLOOD FILTER

BACKGROUND OF THE INVENTION

This invention relates to a blood filter for removing foreign matters and bubbles from blood passing an extracorporeal blood circuit including an artificial heart-lung or pump-oxygenator, an artificial kidney or dialyzator, and a device for separating blood cell and plasma components, and more particularly, to a blood filter having improved debubbling capacity.

A number of blood filters are known in the art. One typical blood filter is disclosed in U.S. Pat. No. 4,411,783. In FIG. 14 of the present drawing, the blood filter generally designated at 100 is illustrated as comprising a cylindrical housing 102 formed of polycarbonate resin, for example, having a blood inlet 105 and a blood outlet 108, and a filter member 109 received in the housing 102 between the inlet 105 and the outlet 108. The filter member 109 is prepared by sandwiching a mesh screen with an opening of 20–50 μm between plastic nets, folding the sandwich in pleats, and mating the ends to form a generally cylindrical filter member. To prevent bubbles from directly passing to the filter member 109, the blood inlet 105 is tangentially connected to the cylindrical housing 102 such that blood B may enter the housing interior in a tangential direction to form a swirl flow therein as shown in FIG. 15 which is a cross section of the blood filter of FIG. 14 taken along lines III—III. It is also known to interpose a continuous foam between the blood inlet and the filter member to prevent bubbles from directly passing to the filter member.

In the blood filter of the above-mentioned type wherein blood B enters the housing 102 through the inlet 105 to form a swirl flow therein, bubbles are removed by virtue of a centrifugal effect that fine bubbles with a small mass entrained in the swirl flow of blood B will collect toward the center of swirl. Since buoyancy applies at all times to bubbles in blood B, separated bubbles will float and collect at an axial top portion of the housing 102 and outflow through a vent 106 at the axial top portion of the housing 102. The filter member 109 removes only those bubbles which are not removed by the buoyancy and the centrifugal force of the swirl flow, that is, bubbles which are not entrained in the swirl flow of blood B. In the above-mentioned modification wherein a continuous foam is present between the inlet and the filter member, the foam removes such bubbles.

In the blood filter 100 mentioned above, however, the inflow of blood which is entering the housing 102 through the inlet 105 directly impinges against a swirl flow of blood which is already whirling in the housing 102 as shown in FIG. 15. Since this causes a disturbance in the blood inflow before the inflow merges with the swirl flow, bubbles are not so smoothly conveyed to the swirl flow of blood. Thus, this blood filter 100 has the drawback that much bubbles reach the filter member 109 because bubbles of a small mass cannot be so effectively separated from blood B by entraining bubbles on the swirl flow of blood and permitting such bubbles to collect toward the swirl center by virtue of a centrifugal effect. Bubbles in blood B impinge against and stick to the filter member 109 and some bubbles then gradually penetrate through the filter member 109 partially under the influence of a pressure variation caused by pulsation of a feed pump. Also, the above-mentioned blood filter of the type using a continuous foam has several problems including adherence of platelets to the foam, damage to cells, an increased pressure loss, and difficulty of debubbling upon priming.

SUMMARY OF THE INVENTION

An object of the present invention is to provide a novel and improved blood filter of relatively simple design exhibiting high debubbling performance while minimizing platelet adherence, cell damage, and pressure loss, and facilitating debubbling upon priming.

According to the present invention, there is provided a blood filter comprising a bubble separating section and a blood filter section disposed below the bubble separating section. The bubble separating section includes a chamber having a generally circular cross section for allowing bubbles to separate from blood, a vent formed at an upper end of the chamber for discharging air, an inlet conduit horizontally extending from the chamber for introducing blood into the chamber, the axis of the inlet conduit extending substantially parallel to a tangent to the generally circular chamber at the connection between the chamber and the inlet conduit, and an inflow portion merging the inlet conduit to the chamber. The blood filter section includes an outlet disposed at a lower end of the filter section for discharging blood and a filter member disposed between the inlet and the outlet. Then the inflow portion introduces incoming blood from the inlet conduit so as to flow as a substantial laminar flow to a swirl blood flow in the chamber and then merge with the swirl flow.

BRIEF DESCRIPTION OF THE DRAWINGS

The above and other objects, features and advantages of the present invention will be better understood from the following description taken in conjunction with the accompanying drawings, in which.

DETAILED DESCRIPTION OF THE PREFERRED EMBODIMENTS

Figure 1:
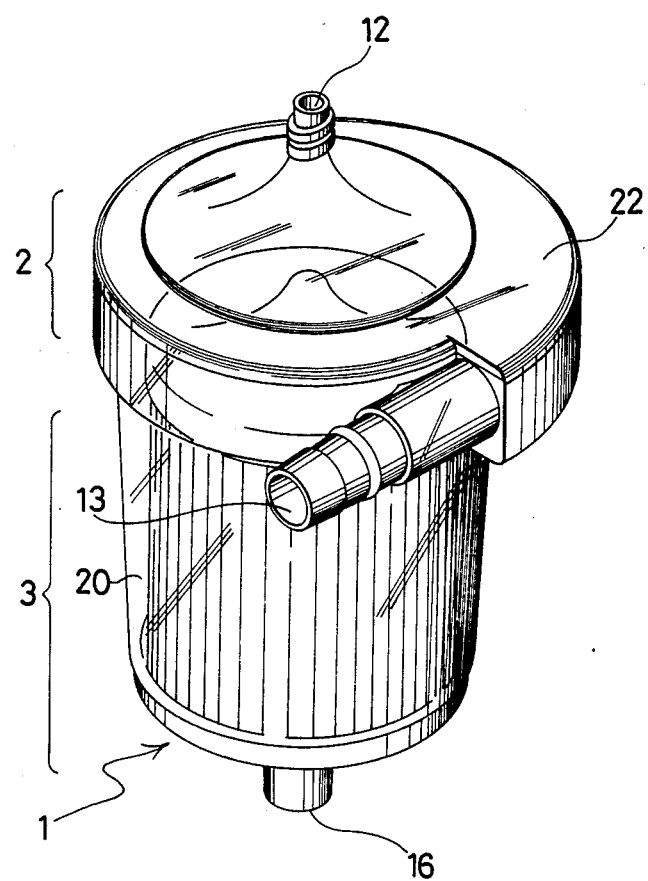
FIG. 1 is a perspective view of a blood filter according to one embodiment of the present invention.

The invention will be described in further detail by referring to several embodiments illustrated in the drawings.

The blood filter according to the present invention is generally designated at 1, which comprises a bubble separating section 2 including chamber 10 having a generally circular cross section for allowing bubbles to separate from blood, a vent 12 formed at an upper end of the chamber 10 for discharging air, an inlet conduit 13 horizontally extending from the chamber 10 for introducing blood into the chamber, the axis of the inlet conduit 13 extending substantially parallel to a tangent to the generally circular chamber 10 at the connection between the chamber and the inlet conduit, and an inflow portion 15 merging the inlet conduit 13 to the chamber 10; and a blood filter section 3 disposed below the bubble separating section 2, including an outlet 16 disposed at a lower end of the filter section for discharging blood and a filter member 18 disposed between the inlet 13 and the outlet 16; whereby the inflow portion 15 introduces incoming blood from the inlet conduit 13 to flow as a substantial laminar flow to a swirl flow of blood in the chamber 10 and then merge with the swirl flow.

One embodiment of the blood filter of the present invention is illustrated by referring to FIGS. 1 to 4.

The blood filter 1 includes a bubble separating section 2 and a blood filter section 3. The bubble separating section 2 includes an upper housing of a generally circular cross section defining a chamber 10 therein for allowing bubbles to separate from blood. The upper housing is a generally cylindrical housing over which a generally conical lid 22 is fitted. A vent 12 is opened at an upper end of the conical lid 22 in communication with the chamber for discharging air. A tubular blood inlet conduit 13 horizontally extends from the side of the upper housing. A blood inflow portion 15 merges the inlet conduit 13 to the chamber 10. The blood filter section 3 includes a generally cylindrical lower housing 20 which is concentrically disposed below and contiguous to the upper housing. An outlet 16 is opened at an axial lower end of the lower housing for discharging blood therefrom. A filter member 18 is received in the lower housing so as to axially extend between the inlet and the outlet.

Figure 2:
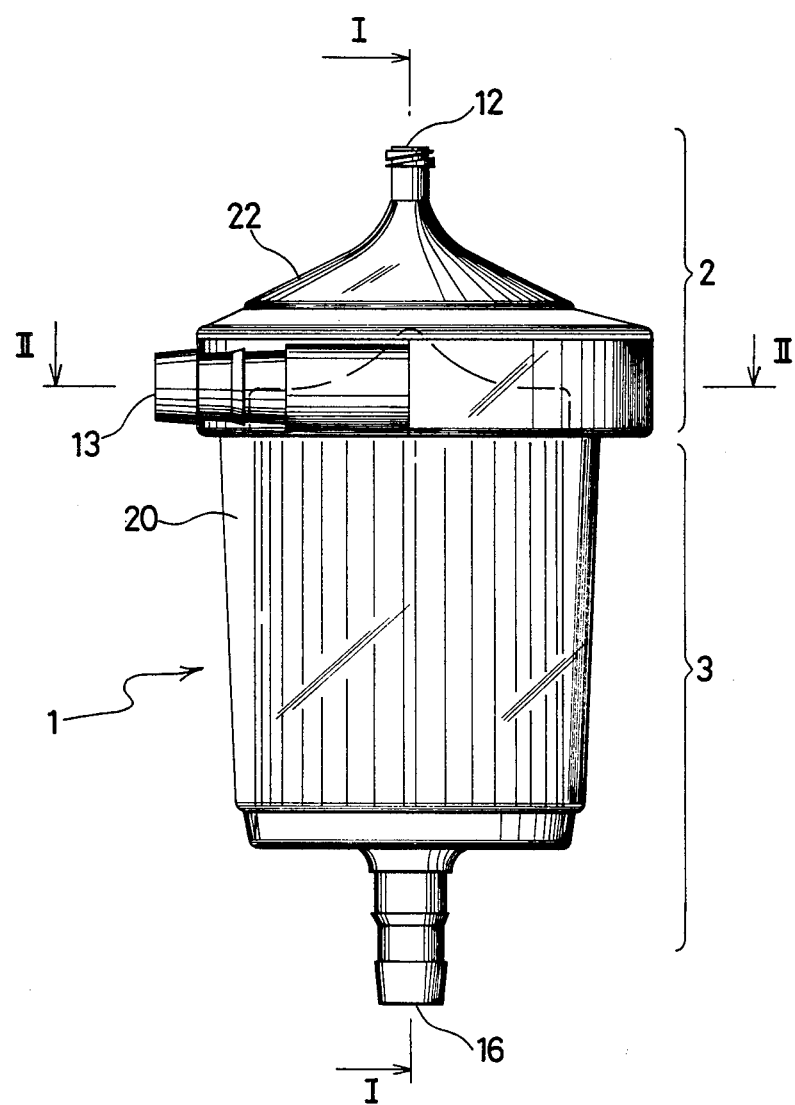
FIG. 2 is a side elevation of the blood filter of FIG. 1.

More particularly, the blood filter 1 according to the embodiment shown in FIGS. 1 to 4 includes an integral housing 20 having an upper opening, and a generally conical lid 22 fitted over the housing to close the opening. The integral housing may be considered as comprising upper and lower housings. The upper housing defines the bubble separating chamber 10 therein and has the inflow portion 15 attached thereto. The lower housing constitutes the filter section 3 with the filter member 18 received therein. The upper housing and the lid 22 define the bubble separating chamber 10. That is, the lid 22 defines an upper portion of the bubble separating chamber 10. The vent 12 is formed at the top of the lid 22 to communicate the chamber 10 to the exterior. The entire housing components including the lid, upper and lower housings may be formed of any desired synthetic resins including polycarbonate, polypropylene, polyethylene, styrene-butadiene (SB) resin, and methylene-butadiene-styrene (MBS) resin. These components are preferably transparent as shown in FIGS. 1 and 2 because easy observation of the contents in the housing is desirable. The upper housing defining the chamber 10 is connected to the lower housing through a step 20a in the illustrated embodiment. It is also possible that the bubble separating section 2 and the blood filter section 3 may have substantially the same diameter so that they are smoothly connected to each other. A tapered connection is also possible. It is to be noted that the blood filter section is omitted in FIG. 4.

The housing 20 at its upper side wall is provided with the blood inlet 13. The inlet 13 has a cylindrical blood introducing conduit 14 which is provided outside the bubble separating chamber 10 and extends substantially parallel to a tangent to a cross sectional circle of the bubble separating chamber 10. The blood inflow portion 15 is connected to the blood introducing conduit 14 at a leading end and to the chamber 10 at a trailing end. The inflow portion 15 has an outer wall 15a whose radial distance from the chamber 10 gradually decreases from the leading end to the trailing end. The inflow portion 15 has the maximum cross sectional area at the connection to the blood introducing conduit 14 and then gradually reduces its cross sectional area or contracts until the inflow portion 15 merges into the upper housing 10b or chamber 10. The inflow portion 15 encloses a portion of the outer circumference of the bubble separating chamber.

Figure 4:
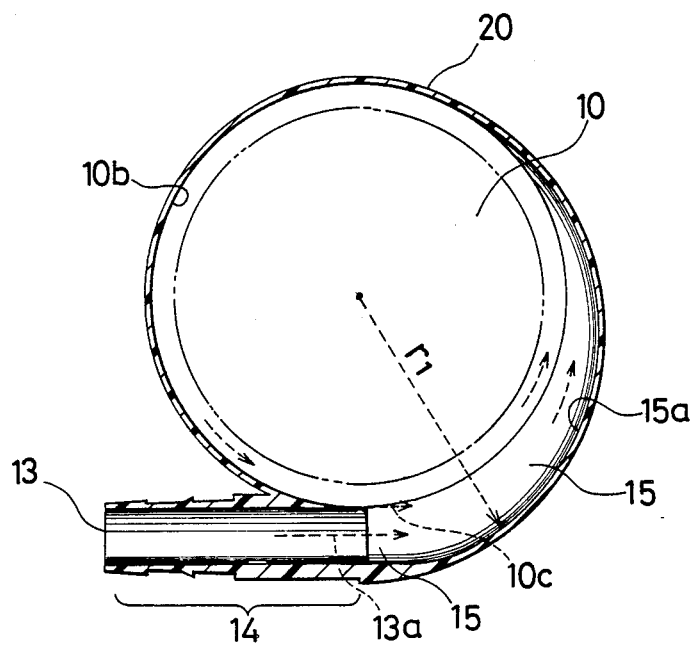
FIG. 4 is a horizontal cross section of the blood filter taken along lines II—II in FIG. 2, with the filter section omitted.

More particularly, the inflow portion 15 has the outer wall 15a on a circle having a radius r1 about a center offset the center of the upper housing as shown in FIG. 4. An inflow of blood is smoothly introduced into the bubble separating chamber 10 over an angle of 90° to 360°, preferably 135° to 225°. The inflow portion 15 is a merging portion where an inflow of blood incoming from the inlet 13 merges with a swirl flow of blood along the inside wall 10b of the upper housing. The axis 13a of the inlet conduit 14 extends substantially parallel to a tangent 10c to the circular cross section of the bubble separating chamber 10. Thus in the inflow portion 15, an inflow of blood incoming from the inlet 13 merges with a blood swirl flow in the chamber such that their streamlines are substantially in parallel to each other, and thus they flow as a substantial laminar flow. The vertical cross section of the inlet 13, the introducing conduit 14 and the inflow portion 15 may be circular or rectangular.

The vent 12 is in communication with the top end of the bubble separating chamber 10. The vent 12 may be provided with valve means such as a three-way cock (not shown). The vent 12 is located at the top of the conical lid 22 or aligned with the axis of the bubble separating chamber 10. The inflow of blood incoming from the inlet 13 to the chamber 10 in a tangential direction thereof at a certain flow velocity forms a swirl flow in the chamber 10 where bubbles centrifugally segregate from the blood, move toward the axial center of the chamber 10, and collect in an upper portion of the chamber 10. Then bubbles may be readily discharged by releasing the vent 12.

The lid 22 is fluid-tightly secured to the upper housing 20 by adhesive bonding, ultrasonic sealing or RF welding.

The filter member 18 is received in the lower housing 20 such that a bubble-containing inflow of blood incoming from the inlet 13 may not directly impinge against the filter member 18.

Figure 3:
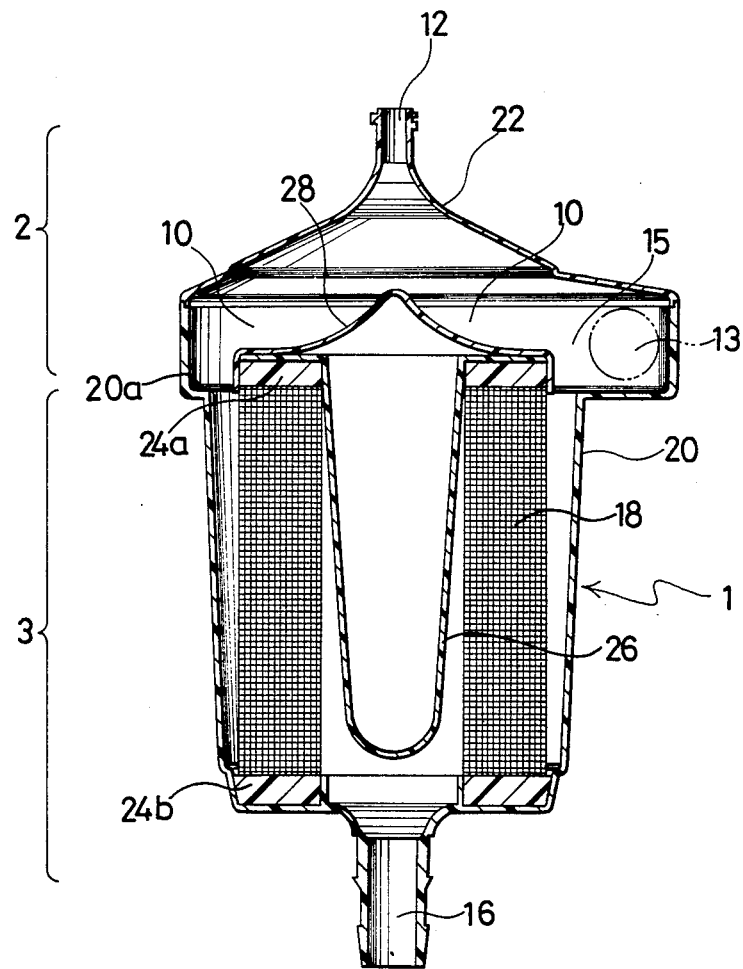
FIG. 3 is a vertical cross section of the blood filter taken along lines I—I in FIG. 2.
Figure 5:
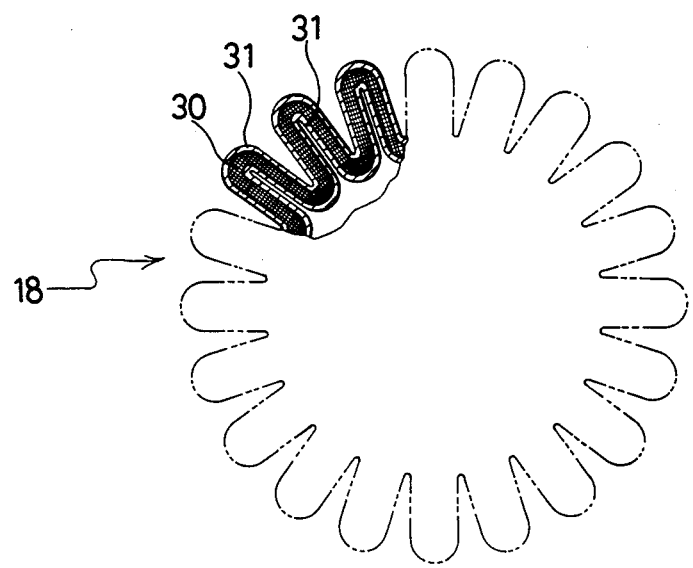
FIG. 5 illustrates partially in cross section the filter member used in FIG. 1.

The filter member 18 is prepared as shown in FIG. 5, by sandwiching a mesh screen 30 with an opening of about 20-50 μm at its opposed major surfaces between plastic nets 31 and 31, folding the sandwich in pleats, rounding the pleated sandwich and mating the ends thereof to form a generally cylindrical filter member. The mesh screen 30 is generally formed of a hydrophobic synthetic resin such as polypropylene, polyethylene, and polyester. The net 31 is also formed of a similar resin such as polypropylene, polyethylene, and polyester. Opposed end portions of the cylindrical filter member 18 are bonded to form seals 24a and 24b (see FIG. 3) by casting any desired potting compounds including polyolefins such as polypropylene and polyethylene, ethylene-vinyl acetate (EVA), polyurethane, styrene-butadiene-styrene (SBS) and silicone rubber and other elastomers. As shown in FIG. 3, the cylindrical filter member 18 is axially received in the housing 20 with one seal 24a at the top and the other seal 24b in close contact with the housing bottom. This construction prevents blood from bypassing to the outlet 16 without passing through the filter member 18. A generally tubular holder 26 having a closed bottom is inserted in a central bore of the filter member 18 to maintain the shape of the filter member. A generally conical closure member 28 is mounted on the top seal 24a of the filter member 18. The filter member 18 removes foreign substances having a relatively large mass, for example, thrombi from a blood flow.

Figure 6:
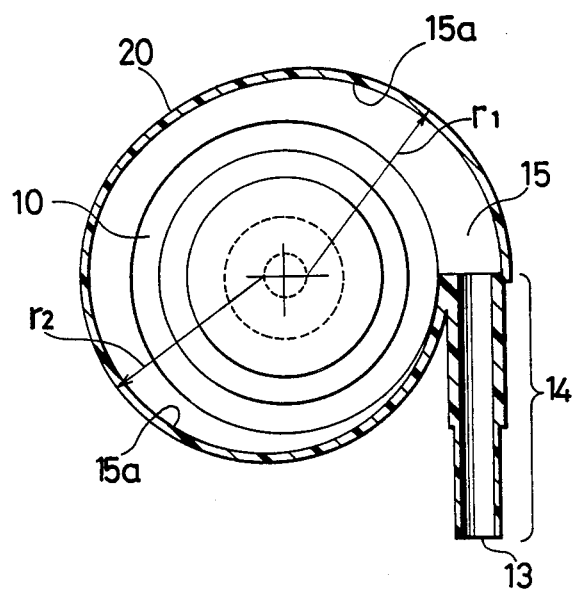
FIGS. 6 and 7 are cross sections similar to FIG. 4, illustrating different embodiments of the present invention.
Figure 7:
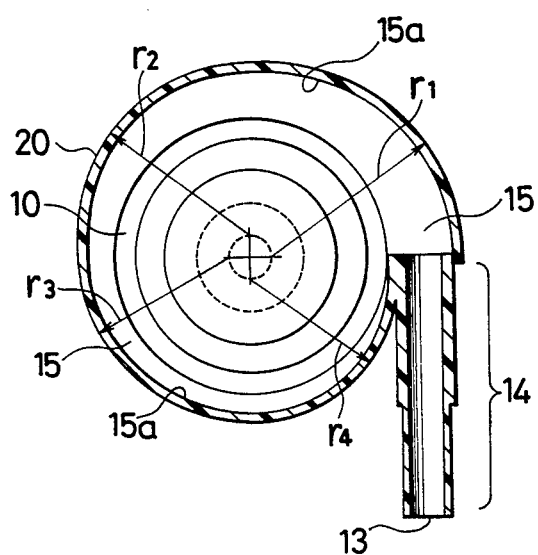

Other embodiments of the blood filter of the present invention are illustrated in FIGS. 6 and 7.

FIGS. 6 and 7 show a cross section of the blood filter taken along an upper horizontal plane similar to FIG. 4, schematically illustrating the blood filter section constituting an internal structure of the filter. The embodiment of FIG. 6 is different from that of FIGS. 1–5 in the design of the blood inflow portion 15. The side wall 15a of the inflow portion 15 encloses approximately less than a half of the circumference of the bubble separating chamber 10 and has a fixed radius r1 in FIG. 4. In the embodiment of FIG. 6, the side wall 15a of the inflow portion 15 encloses approximately the entire circumference of the bubble separating chamber 10. The side wall 15a consists of two semi-circular segments of different curvatures, a first segment of 180° having a first radius r1 and a second segment of 180° having a second radius r2, the first radius being larger than the second radius (r1>r2). Thus, the inflow portion 15 in this embodiment is relatively long in a circumferential direction. That is, the merge line between the inflow portion 15 and the chamber 10 is long. A blood inflow from the inlet 13 will more gradually merge with a swirl flow of blood in the chamber 10.

The embodiment of FIG. 7 is similar to that of FIG. 6, but different from the latter in that the side wall 15a of the inflow portion 15 consists of four quarter-circular segments of different curvatures, that is, first, second, third and fourth segments of each 90° having different radii r1, r2, r3, and r4 (r1>r2>r3>r4). The distance between the side wall 15a and the contour of the bubble separating chamber 10 gradually decreases from the leading end to the trailing end.

The remaining construction and operation of the embodiments shown in FIGS. 6 and 7 are the same as in FIGS. 1 to 5.

The blood filter of the present invention is described only in conjunction with its removal of bubbles from blood. The invention is not limited to blood, and may be applied to any liquid medicaments.

The operation of the blood filter of the present invention will be illustrated in connection with the embodiment shown in FIGS. 1 to 4 while also referring to FIG. 8.

Figure 8:
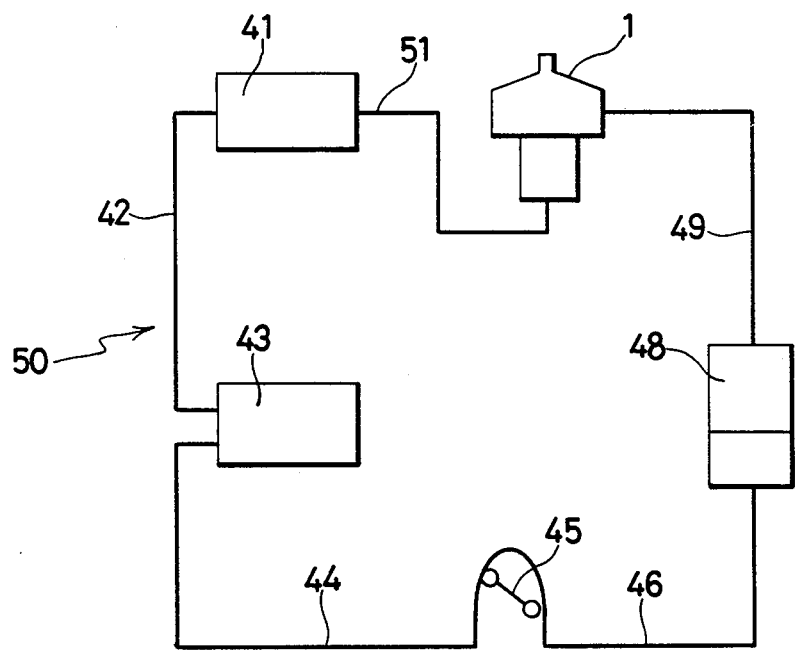
FIG. 8 is a schematic view showing an artificial heart-lung circuit to which the blood filter of the present invention is applied.

The blood filter 1 is used in an artificial heat-lung circuit 50 as shown in FIG. 8, for example, for the purpose of removing bubbles and foreign substances from blood. The circuit 50 includes a patient 41, a blood reservoir 43, a pump 45, a heat exchanger/oxygenator 48, and the blood filter 1 connected in this order. More particularly, the vein of the patient 41 is connected to the reservoir 43 via a line 42. The reservoir 43 is connected to the pump 45 via a line 44, to the oxygenator 48 via a line 46, and then to the inlet of the blood filter 1 via line 49. The outlet of the blood filter 1 is connected to the aorta of the patient 41 via a line 51. Blood in the reservoir 43 is pumped to the inlet 13 of the filter 1 via the communicating lines by the pump 45. Since the pump 45 feeds blood under pressure, a blood flow at a certain flow speed reaches the inflow portion 15 through the inlet 13 and the introducing conduit 14 (see FIGS. 3 and 4). Since the inflow portion 15 is designed such that its side wall 15a gradually approaches the bubble separating chamber 10, the blood incoming from the inlet 13 passes the inflow portion 15 as a laminar flow with a blood swirl flow in the chamber 10 and then merges with the latter. The blood incoming from the inlet 13 does not directly impinge against the existing flow of blood swirling in the chamber 10 and the filter section 3. The newly introduced blood passes along the side wall 15a of the housing 20 defining the inflow portion 15 while being converted into a swirl flow and then merges with the existing flow of blood swirling in the chamber 10 and the filter section 3. Therefore, the newly introduced blood causes no substantial disturbance to the existing swirl flow in the chamber 10. Since the blood which has just been introduced from the inlet does not substantially interfere with the existing swirl flow in the filter vessel, few bubbles in the newly introduced blood will migrate to the filter member 18. While blood flows in the chamber 10 as a swirl flow, bubbles of a small mass in the blood migrate toward the center of swirl due to a centrifugal force of swirl and at the same time, move upward due to buoyancy acting in blood, eventually collecting in a central upper portion of the chamber 10. The thus collected bubbles or air is discharged outside through the vent 12. The blood entering the filter section 3 is filtered of foreign substances. The filtered blood is fed back to the aorta of the patient 41 from the outlet 16 of the blood filter 1 through the line 51.

An example of the blood filter of the present invention is given below by way of illustration and not by way of limitation.

EXAMPLE

Figure 9:
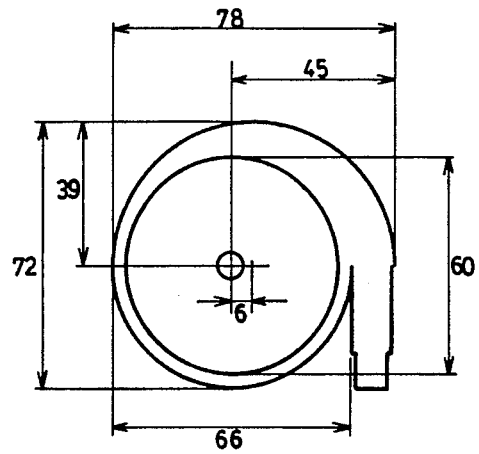
FIGS. 9 and 10 are schematic horizontal and vertical cross-sectional views showing the interior configuration and dimensions of the blood filter fabricated in Example.
Figure 10:
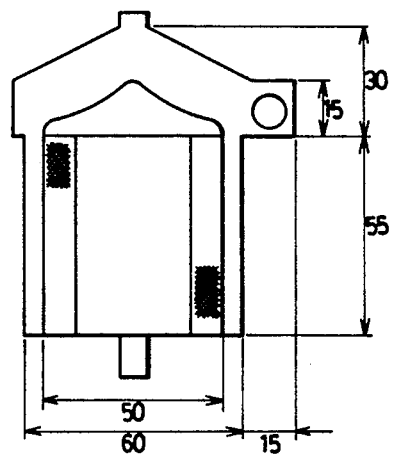

A housing and a lid were used having an interior configuration and dimensions as shown in FIGS. 9 and 10. The housing defined an interior volume of about 200 ml when the lid was mounted thereon. A filter member was a generally cylindrical mesh having an opening of 40 μ, a pitch of 12 mm, an effective height of 68 mm, and pleat number 40 (manufactured by Izumi K. K., trade name T-350) which was prepared by sandwiching a polyester mesh between a pair of polyester nets, and pleating and rounding the laminate as shown in FIG. 5.

The filter member had an outer diameter of 50 mm as shown in FIG. 9 and an effective surface area of about 650 cm². The filter member at upper and lower ends was bonded with a polyurethane potting compound. A tubular holder in the form of a tapered tube having a closed bottom and an annular flange around an upper opening thereof was inserted into a central bore of the filter member from above. A conical closure member was secured to the upper end of the filter member so as to cover the holder. The conical closure member had a diameter as shown in FIG. 9. The lower end of the filter member was secured to the bottom inside of the housing with a polyurethane adhesive. The lid was secured to the housing, completing the blood filter of the design shown in FIGS. 1 to 5.

COMPARATIVE EXAMPLE

Figure 11:
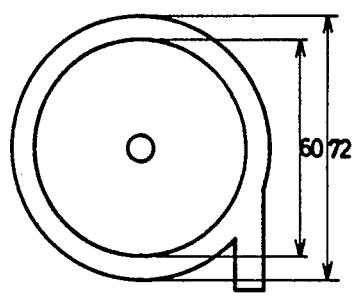
FIGS. 11 and 12 are schematic horizontal and vertical cross-sectional views showing the interior configuration and dimensions of the blood filter fabricated in Comparative Example.
Figure 12:
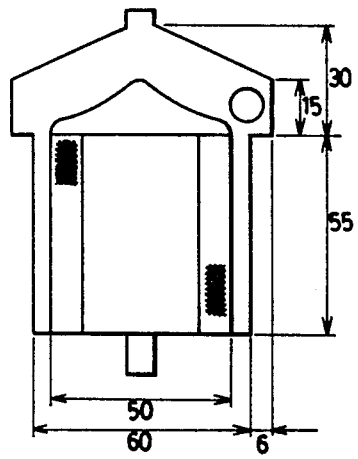
Figure 15:
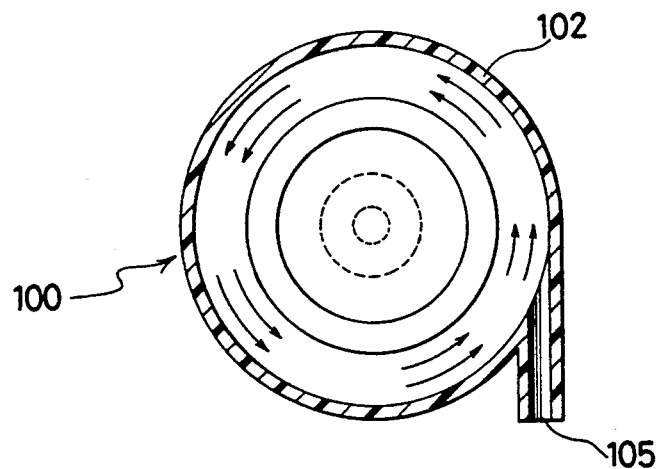
FIG. 15 is a horizontal cross section of the prior art blood filter taken along lines III—III in FIG. 14.
Figure 14:
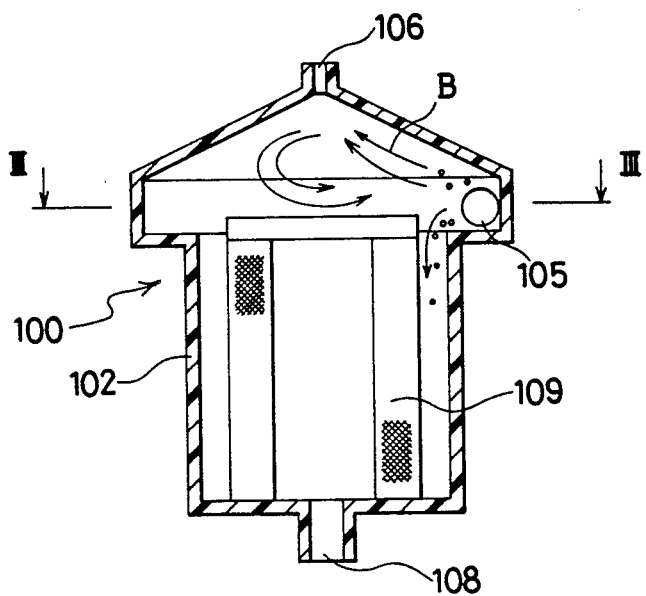
FIG. 14 is a vertical cross section of a prior art blood filter.

A housing and a lid were used having an interior configuration and dimensions as shown in FIGS. 11 and 12. The housing defined an interior volume of about 200 ml when the lid was mounted thereon. A filter member was the same as used in Example. The filter member had an outer diameter of 50 mm as shown in FIG. 12 and an effective surface area of about 650 cm². The filter member at upper and lower ends was bonded with a polyurethane potting compound. The filter assembly was completed by the same procedure as in Example by inserting a tubular holder into a central bore of the filter member and securing a conical closure member to the upper end of the filter member so as to cover the holder. The lower end of the filter member was secured to the bottom inside of the housing with a polyurethane adhesive. The lid was secured to the housing, completing a comparative blood filter.

EXPERIMENT

An experiment was done with the blood filters fabricated in Example and Comparative Example.

Figure 13:
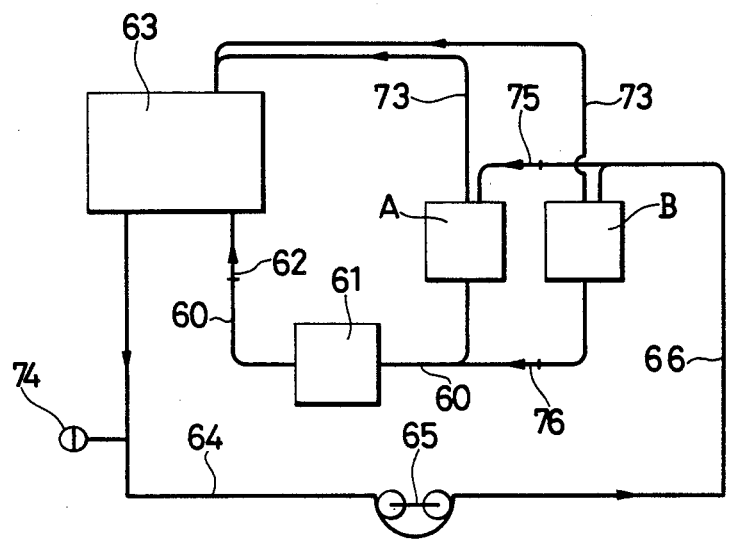
FIG. 13 is a schematic view showing a test circuit used to determine the performance of a blood filter of the invention and a comparative filter.

The experiment was carried out by incorporating the blood filter in a blood circuit as shown in FIG. 13.

Briefly stated, the circuit includes a blood reservoir 63, a pump 65, parallel connected filters A and B, and a ultrasonic bubble detector 61. The reservoir 63 is connected to a suction port of the pump 65 via a line 64. A discharge port of the pump 65 is connected to inlets of the parallel filters A and B via a branched line 66. Outlets of the filters A and B are connected to the detector 61 via a branched line 60. The detector 61 is connected to the reservoir 63 via a line 60 and a clamp 62. Vents of the filters are connected to the reservoir 63 via purge lines 73. The line 64 is tapped with an air injector 74 for blowing air into blood. The lines 66 and 60 are provided with clamps 75 and 76 so as to switch a blood line between filters A and B. It is to be noted that A designates the blood filter of Example and B is the blood filter of Comparative Example.

In the experiment, bovine blood (Ht 35%) was used. Both the blood filters of Example and Comparative Example were designed such that they filtrated bovine blood under an average pressure of 200±20 mmHg at the upstream side of the filter. The pump was designed to pump blood at a flow rate of 4 liter/min. Air was blown into blood at a rate of 20 ml/min. by means of the air injector 74. Bubbles in blood were measured using the ultrasonic bubble detector (Hps-1000, manufactured by Microemboli Detection System Extracorporeal Technologies, Inc., Indianapolis, U.S.A.). The priming quantities required for the blood filters of Example and Comparative Example were substantially equal.

Bubbles were counted in the blood flows which had passed the blood filters of Example and Comparative Example. The bubble measurement was made 600 times per 30 seconds. The count is a value of integration of maximum bubble diameters sensed upon ultrasonic pulse exposure (an average of five measurements). Since no accurate count could be obtained as to bubbles having a small diameter of less than 20 μm, the corresponding data was omitted. The results are shown in Table 1.

TABLE 1

| Bubble size (μm) | Filter A (count) | Filter B (count) |
|---|---|---|
| — | — | — |
| 20–25 | 104 | 161 |
| 25–30 | 36 | 69 |
| 30–35 | 5 | 22 |
| 35–40 | 1 | 4 |
| 40–45 | 0 | 1 |

It is apparent that the structure of the present invention is effective to assist the filter in removing bubbles from blood.

As is apparent from the above teaching, the blood filter of the present invention is designed as comprising a bubble separating section including a chamber having a generally circular cross section for allowing bubbles to separate from blood, a vent formed at an upper end of the chamber for discharging air, an inlet conduit horizontally extending from the chamber for introducing blood into the chamber, the axis of said inlet conduit extending substantially parallel to a tangent to the generally circular chamber at the connection between the chamber and the inlet conduit, and an inflow portion contiguous to the inlet conduit; and a blood filter section disposed below the bubble separating section, including an outlet disposed at a lower end of the filter section for discharging blood and a filter member disposed between the inlet and the outlet; whereby the inflow portion leads blood incoming from the inlet conduit so as to flow as a substantial laminar flow to a swirl flow of blood in the chamber and then merge with the swirl flow. At the interface between the inflow portion and the chamber, the blood newly introduced through the inlet conduit does not directly strike against the swirl flow of blood which has been whirling in the chamber. The newly introduced blood first passes as a substantial laminar flow to the existing swirl flow at the leading end of the inflow portion, then gradually converts into a swirl flow as it advances along the side wall defining the inflow portion, and finally merges to the existing swirl flow in the chamber until it reaches the trailing end of the inflow portion. The blood inflow gives rise to no disturbance to the existing swirl flow of blood in the chamber. Since the blood which has just been introduced from the inlet conduit does not substantially interfere with the existing flow of blood in the chamber, most bubbles in the newly introduced blood are readily entrained to the swirl flow while few bubbles reach the filter member. Then bubbles having a small mass will migrate toward the center of swirl due to a centrifugal force of swirl while emerging upward due to buoyancy, thus collecting at an upper portion of the chamber. The thus collected bubbles are readily discharged exterior of the housing through the vent.

The blood filter of the invention has a high debubbling capacity irrespective of a simple structure and is remarkably improved over a prior art blood filter using a continuous foam for debubbling with respect to platelet adherence, cell damage, pressure loss and debubbling upon priming operation.

Obviously modifications and variations of the present invention are possible in the light of the above teachings. It is therefore to be understood that within the scope of the appended claims the invention may be practiced otherwise than as specifically described.

We claim:

1. A blood filter, comprising:
   a filter housing;
   said housing forming a bubble separating section including
      a chamber defined by said housing and having a generally circular cross section for allowing bubbles to separate from blood when introduced into said chamber,
      a vent formed at upper end of the housing to communicate with the chamber for discharging air from said bubbles,
      an inlet conduit horizontally extending from the housing for introducing blood into the chamber, the axis of said inlet conduit extending substantially parallel to a tangent line of the generally circular chamber in the vicinity of the connection between the chamber and the inlet conduit, the inlet conduit axis being outside said chamber and being offset a certain distance from said tangent line in a plane perpendicular to the axis of said chamber, and
      said housing defining an inflow portion merging the inlet conduit to the chamber, and
   said housing forming a blood filter section disposed below said bubble separating section, including
      an outlet disposed at a lower end of the housing for discharging blood, and
      a filter member disposed in said housing between the inlet conduit and the outlet,
   wherein said inflow portion is contoured so that said inflow portion introduced incoming blood from the inlet conduit to flow as a substantial laminar flow up to an existing swirl blood flow in the chamber, and to merge with the swirl blood flow without substantial disturbance of the swirl blood flow.

2. The blood filter of claim 1 wherein a side wall part of the housing defining said inflow portion is contiguous to the inlet conduit at a leading end and to the chamber at a trailing end, and the side wall part encloses at least a portion of the generally circular chamber of the bubble separating section, and the radial distance between the side wall part and the chamber in the plane perpendicular to the axis of the chamber, gradually decreases from the leading end to the trailing end.

3. The blood filter of claim 2 wherein said bubble separating section further includes a generally conical lid part of the housing for covering the chamber, the vent being provided at the top of said lid part.

4. The blood filter of claim 1 wherein said bubble separating section further includes a generally conical lid part of the housing for covering the chamber, the vent being provided at the top of said lid part.

5. The blood filter of claim 2, wherein said side wall part extends over an angle in the range of from 90° to 360° about the axis of said chamber.

6. The blood filter of claim 2, wherein said side wall part extends over an angle in the range of from 135° to 225° about the axis of said chamber.

7. The blood filter of claim 2, wherein said side wall part extends over a path that encloses about 360° of said chamber, a first half of said path being defined by a first radius and a second half of said path being defined by a second radius smaller than said first radius.

8. The blood filter of claim 2, wherein said side wall part extends over a path that encloses about 360° of said chamber, a first quarter of said path being defined by a first radius r1, a second quarter of said path being defined by a second radius r2, a third quarter of said path being defined by a third radius r3, a fourth quarter of said path being defined by a fourth radius 4, with the relation $r1 > r2 > r3 > r4$.

* * * * *

UNITED STATES PATENT AND TRADEMARK OFFICE
CERTIFICATE OF CORRECTION

PATENT NO.　：　4,919,802

DATED　　　：　April 24, 1990

INVENTOR(S)：　KATSURA, Yoshiro

It is certified that error appears in the above-identified patent and that said Letters Patent is hereby corrected as shown below:

Column 10, line 2 (Claim 1):

change "introduced" to --introduces--.

Signed and Sealed this

Eighth Day of September, 1992

Attest:

DOUGLAS B. COMER

Attesting Officer

Acting Commissioner of Patents and Trademarks